(12) United States Patent
Durst et al.

(10) Patent No.: US 8,903,043 B2
(45) Date of Patent: Dec. 2, 2014

(54) METHOD FOR CORRECTING TIMING SKEW IN X-RAY DATA READ OUT OF AN X-RAY DETECTOR IN A ROLLING SHUTTER MODE

(75) Inventors: Roger D Durst, Middleton, WI (US); Joerg Kaercher, Madison, WI (US); Gregory A Wachter, Sun Prairie, WI (US); John L Chambers, Jr., Woodville, OH (US)

(73) Assignee: Bruker AXS, Inc., Madison, WI (US)

( * ) Notice: Subject to any disclaimer, the term of this patent is extended or adjusted under 35 U.S.C. 154(b) by 529 days.

(21) Appl. No.: 13/279,393

(22) Filed: Oct. 24, 2011

(65) Prior Publication Data

US 2013/0103339 A1   Apr. 25, 2013

(51) Int. Cl.
  *G01N 23/20*   (2006.01)
  *G01N 23/207*  (2006.01)
(52) U.S. Cl.
  CPC .................................. *G01N 23/207* (2013.01)
  USPC .............................................. 378/73; 378/70
(58) Field of Classification Search
  USPC ................................................ 378/70, 73, 81
  See application file for complete search history.

(56) References Cited

U.S. PATENT DOCUMENTS

| 7,298,401 | B2 | 11/2007 | Baer |
| 7,667,740 | B2 | 2/2010 | Hofer |
| 7,720,309 | B2 | 5/2010 | Sasaki |
| 2005/0058247 | A1* | 3/2005 | Taguchi et al. ................. 378/71 |
| 2005/0084065 | A1* | 4/2005 | Taguchi .......................... 378/70 |
| 2008/0144964 | A1 | 6/2008 | Soinjo |
| 2010/0039542 | A1 | 2/2010 | Shah |
| 2010/0329657 | A1 | 12/2010 | Hosoi |

OTHER PUBLICATIONS

Chun, J., Junh, H. and Kyung, C.-M., "Suppressing Rolling Shutter Distortion of CMOS Sensors by Motion Vector Detector", IEEE Transactions on Consumer Electronics, v.54, n. 4, pp. 1479-1487 (2008).
Heflin, B., Scheirer, W. and Boult, T., "Correcting Rolling-Shutter Distortion of CMOS Sensors Using Facial Feature Detection", Biometrics: Theory Applications and Systems (BTAS), 2010 Fourth IEEE International Conference on , Sep. 2010, p. 1-6.
Kabsch, W., "Evaluation of Single-Crystal X-ray Diffraction Data from a Position-Sensitive Detector", Journal of Applied Crystallography v. 21, pp. 916-924 (1988).
T. He, et al., A large area X-ray imager with online linearization and noise suppression, Proceedings of the SPIE, Aug. 21, 2011, pp. 1-8, vol. 8142.

(Continued)

*Primary Examiner* — Hoon Song
(74) *Attorney, Agent, or Firm* — Robic, LLP (57) ABSTRACT

In an X-ray detector operating in a rolling shutter read out mode, by precisely synchronizing sample rotation with the detector readout, the effects of timing skew on the image intensities and angular positions caused by the rolling shutter read out can be compensated by interpolation or calculation, thus allowing the data to be accurately integrated with conventional software. In one embodiment, the reflection intensities are interpolated with respect to time to recreate data that is synchronized to a predetermined time. This interpolated data can then be processed by any conventional integration routine to generate a 3D model of the sample. In another embodiment a 3D integration routine is specially adapted to allow the time-skewed data to be processed directly and generate a 3D model of the sample.

11 Claims, 4 Drawing Sheets

(56) References Cited

OTHER PUBLICATIONS

C. Bronnimann, et al., Continuous sample rotation data collection for protein crystallography with the PILATUS detector, Nuclear Instruments and Methods in Physics Research A, Sep. 1, 2003, pp. 24-28, vol. 510.

W. Kabsch, Evaluation of Single-Crystal X-ray Diffraction Data from a Position-Sensitive Detector, Journal of Applied Crystallography, Dec. 1, 1988, pp. 916-924, vol. 21.

* cited by examiner

METHOD FOR CORRECTING TIMING SKEW IN X-RAY DATA READ OUT OF AN X-RAY DETECTOR IN A ROLLING SHUTTER MODE

BACKGROUND

This invention relates to X-ray diffraction systems. X-ray diffraction is a non-destructive technique for the qualitative and quantitative analysis of crystalline material samples, which are generally provided in the form of single crystals. In accordance with this technique, an X-ray beam is generated by an X-ray tube with a stationary anode, by a conventional rotating anode X-ray source or by a synchrotron source and directed toward the material sample under investigation. When the X-rays strike the sample, they are diffracted according to the molecular structure of the sample.

Figure 1:
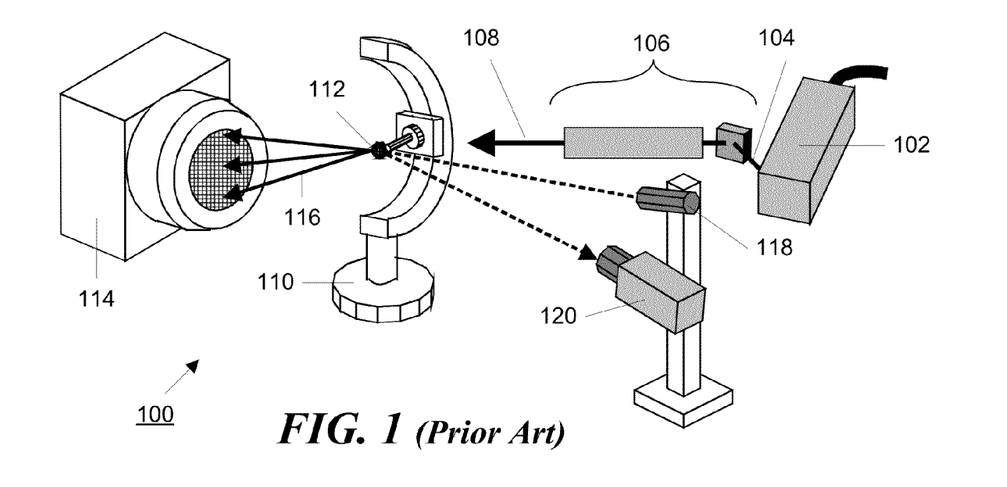
FIG. 1 shows a conventional laboratory X-ray diffraction system.

A typical laboratory system 100 for performing single crystal diffraction experiments normally consists of five components as shown in FIG. 1. The components include an X-ray source 102 that produces a primary X-ray beam 104 with the required radiation energy, focal spot size and intensity. X-ray optics 106 are provided to condition the primary X-ray beam 104 to a conditioned, or incident, beam 108 with the required wavelength, beam focus size, beam profile and divergence. A goniometer 110 is used to establish and manipulate geometric relationships between the incident X-ray beam 108, the crystal sample 112 and the X-ray detector 114. The incident X-ray beam 108 strikes the crystal sample 112 and produces diffracted X-rays 116 which are recorded in the detector 114. A sample alignment and monitor assembly comprises a sample illuminator 118 that illuminates the sample 112 and a sample monitor 120, typically a video camera, which generates a video image of the sample to assist users in positioning the sample in the instrument center and monitoring the sample state and position.

The goniometer 110 allows the crystal sample 112 to be rotated around one or more axes. Precise crystallography requires that the sample crystal 112 be aligned to the center of the goniometer 110 and maintained in that center when rotated around the goniometer rotational axes during data collection. During exposure, the sample (a single crystal of the compound of interest) is rotated in the X-ray beam 108 through a precise angular range with a precise angular velocity. The purpose of this rotation is to predictably bring Bragg angle reflections from each atomic plane of the sample into resonance with the incident beam 108 for the same period of time. This recording process produces a set of data, called a "frame", which at the end of the exposure time is stored in the detector.

Current generation X-ray area detectors used for crystallography, including charge coupled devices (CCDs) and Image Plates, have a finite read out dead time (typically on the order of 1-100 seconds) during which the integrated detector data is read out of the detector and no new data can be acquired. This so called "read out dead time" can significantly decrease the effective collection efficiency of the detector. For example, with modern sources and detectors it is not uncommon to acquire frames with exposure times on the order of one second. With a readout dead time of five seconds, the detector is completely idle (collecting no X-ray intensity data) 80% of the time.

Another deleterious effect of readout dead time is degradation of the data quality due to timing jitter of the mechanical components. During the read out dead time, a shutter (not shown in FIG. 1) in front of the X-ray source 102 is closed to shut off X-ray flux in the X-ray beam 108, the goniometer 110 is stopped and the data from the frame just acquired is read out. After the data is read out, the goniometer 110 is restarted, the shutter is reopened and the next frame of data is acquired. This process requires precise synchronization between the detector 114, the shutter and the goniometer 110. Of course, these mechanical components can only be synchronized with a finite precision and thus timing jitter on the order of 10 msec is typically seen. This timing jitter leads directly to errors in the measured X-ray intensities. For example, for frames acquired with a one second exposure time, a 10 msec jitter leads to a 1-2% error. Thus, timing jitter can be one of the most important error sources in the crystallographic measurement.

Figure 2A:
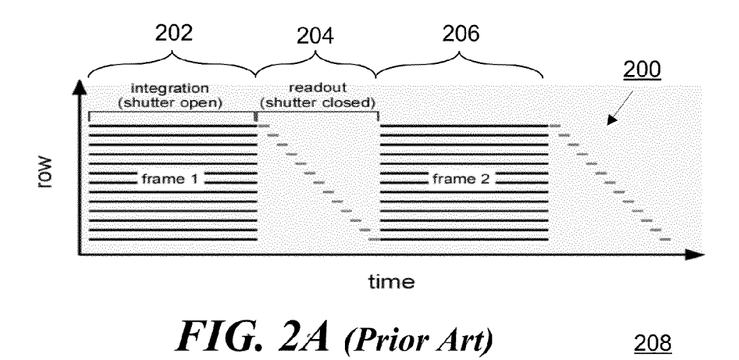
FIG. 2A is a schematic diagram representing data integration and readout sequences per row versus time in a shuttered readout mode for a conventional CCD detector.

This conventional frame-by-frame readout mode is shown schematically in FIG. 2A, which shows the readout of a CCD detector. A CCD detector is comprised of rows of MOS (Metal-Oxide Semiconductor) capacitors. FIG. 2A is a plot 200 that shows the CCD row number on the vertical axis versus time on the horizontal axis. During exposure or integration time 202, all CCD rows acquire data. Then, during readout time 204, each CCD row is sequentially readout until all rows have been readout. The process is then repeated with all CCD rows acquiring data during integration time 206. Depending on the actual detector, readout time 204 could be the same as, or much longer than, integration times 202 and 206. It would obviously be highly advantageous to operate the detector and goniometer in a continuous scan mode wherein the goniometer simply rotates the sample at a constant angular velocity and the detector acquires frames without any readout dead time as this would increase the efficiency of the detector and also essentially eliminate the timing jitter errors. A continuous scan mode is impossible with conventional detectors such as full frame CCDs or Image Plates. However, such a mode is possible with some new types of detectors. CMOS detectors, in particular, have the capability to run continuously with no dead time in either an electronic "global shutter" mode or a "rolling shutter" mode.

In a CMOS detector running in a global shutter mode, at the end of integration, all the pixels in an acquired frame are moved into readout buffers and data in the readout buffers is read out during the acquisition of the next frame. However, detectors running in global shutter mode typically have higher noise and lower quantum efficiency due to the extra transistors required to implement a readout buffer for each pixel.

In contrast, in a rolling shutter mode, the X-ray beam 108 is not shuttered and the goniometer 100 runs continuously. Each pixel in a row is simply readout, in turn, and then reset. That pixel then begins acquiring new data. After the last pixel in a row is readout, the first pixel in the next row is readout, etc. In this case, the entire detector can be readout with no dead time between frames. The rolling shutter mode has the advantage that it is simpler to implement and has lower noise and higher quantum efficiency than the global shutter mode.

Figure 2B:
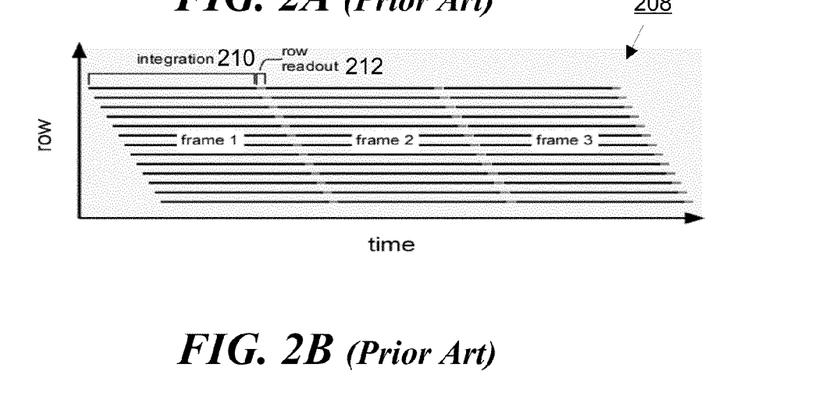
FIG. 2B is a schematic diagram representing data integration and readout sequences per row versus time in a rolling shutter readout mode for a CMOS detector.

However, since the rows are readout sequentially, readout of a row cannot start until all pixels from the prior row have been readout. Consequently, there is a time skew in the readout starting time of each row in a frame. This time skew is equal to the sum of the readout times for each pixel in a row (called the row readout time). This type of operation is illustrated in FIG. 2B, which is a plot 208 that shows the CMOS row number on the vertical axis versus time on the horizontal axis. During data acquisition, each row acquires data during an integration time 210 and reads the data out as indicated by the cumulative row readout time 212. Thus, the next row readout starting time is delayed by this amount of time. Since the first row in a frame cannot be readout until readout of the last row of the frame has completed, after the first row has been readout, there is a delay until the next subsequent readout of that row.

The effect of image skew in a sensor with a rolling shutter read out is well known problem, and there have been a significant number of publications and patents devoted to correcting for these time skew effects. However, the primary focus of the scientific literature and the patent literature is the correction of motion artifacts in a CMOS sensor. That is, when an object moves relative to the camera during a rolling shutter readout the resulting image is distorted due to the time delay effects described above.

For example, an article entitled "Suppressing Rolling Shutter Distortion of CMOS Sensors by Motion Vector detector", Jung-Bum Chun, H. Jung and C.-M. Kyung *IEEE Transactions on Consumer Electronics*, v. 54, n. 4, p. 1479 (2008) describes this effect and how the distortion can be detected and corrected using a motion vector approach. U.S. Patent application No. 2008/0144964 A1 discloses a similar method in which a mathematical model of the motion in an image is constructed and then used to correct for the image distortion caused by a rolling shutter. U.S. Pat. No. 7,720,309 describes detecting similar image elements in adjacent images in rolling shutter video to create a motion matrix which can be used to correct for the "bending" effects caused by a rolling shutter readout. An article entitled "Correcting Rolling-Shutter Distortion of CMOS Sensors using Facial Feature Detection" B. Heflin, W. Scheirer and T. Boult, *Fourth IEEE International Conference on Biometrics: Theory Applications and Systems* (BTAS), p. 1-6 (September 2010) describes using facial feature recognition to detect and correct for image distortion in facial photos. U.S. Patent Publication No. 2010/0329657 describes the use of a second shutter or a flash, synchronized with the camera readout, to eliminate or reduce the motion skew of a fast moving object when imaged with a rolling shutter.

However, these publications all describe how a rolling shutter distorts the image of a moving object and how this distortion can be corrected. An x-ray diffraction system is fundamentally different. The image in this case does not move at all. Rather, the Bragg refection positions are fixed with respect to the sensor but the intensities of the reflections change with time. None of the image motion correction algorithms described in the literature above addresses this situation.

Other authors have looked at correcting for changes in lighting during a rolling shutter readout. For example, U.S. Pat. No. 7,667,740 describes a method for eliminating modulation effects in CMOS sensors caused by using a rolling shutter in an environment illuminated by lighting with 50 or 60 Hz flicker. This is accomplished by creating a model of the illumination modulation and using this to correct the intensity of each row for the change in illumination. However, this approach is not directly applicable to the case of X-ray diffraction as described above since the X-ray diffraction intensities do not follow a simple repetitive modulation as described by Hofer.

U.S. Pat. No. 7,298,401 discloses a technique where the average row intensity is used to estimate a periodic flicker function which can then be used to correct images collected in an environment with changing ambient illumination. Again, this approach assumes a periodic change in illumination and is thus not applicable to the case of X-ray diffraction as described above.

Similarly, U.S. Patent Publication No. 2010/0039542 describes an imaging sensor which incorporates a separate "flicker sensor" that detects changes in the ambient illumination (such as, again, the 50/60 Hz modulation in fluorescent lights) and uses this to correct for the intensity of the image on a row by row basis. However, in the case of X-ray diffraction, there is no comparable change in the overall signal (rather, it is only the local diffracted signals that change) so this approach is not applicable.

Figure 3A:
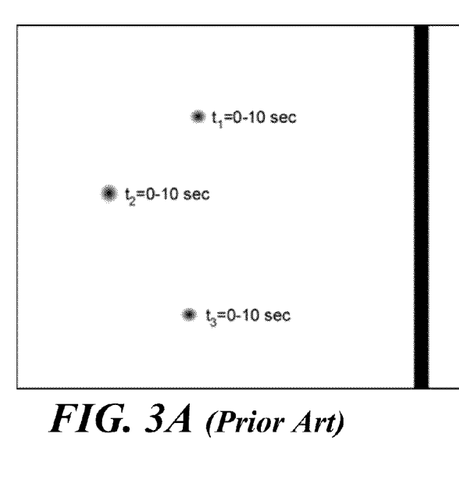
FIG. 3A shows X-ray data from three Bragg reflections acquired on a conventional X-ray detector using a shutter to block the X-ray beam during readout with integration times shown next to each reflection.
Figure 3B:
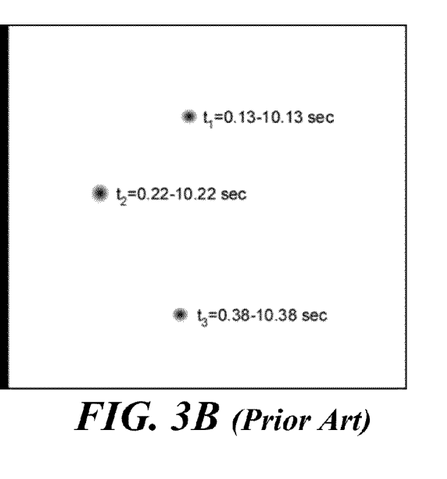
FIG. 3B shows X-ray data from the same three Bragg reflections as shown in FIG. 3A acquired on a CMOS X-ray detector using a rolling shutter mode with integration times shown next to each reflection.

More specifically, in a quantitative application, such as an X-ray diffraction application, it is necessary to precisely compensate for the time skew in the resulting images when using the rolling shutter data acquisition mode. The reason for this compensation is shown schematically in FIGS. 3A and 3B. FIG. 3A shows X-ray data from three Bragg reflections acquired on a conventional X-ray detector using a shutter to block the X-ray beam during readout. Each reflection 300, 302 and 304 is integrated for precisely the same time interval (0-10 seconds in this case) as noted next to the reflection. When data is acquired from the same three reflections with a detector operating in rolling shutter mode, the pattern looks very similar as shown in FIG. 3B with three reflections 306, 308 and 310. The Bragg reflections 306, 308 and 310 do not move with respect to the CMOS detector array (as, for example, would the image of a speeding baseball). In particular, there is no spatial distortion since the positions of the reflections are static with respect to the detector surface. However, each reflection in the image is integrated for a slightly different time interval as noted next to each reflection; this different time interval results in a timing skew.

In order to use diffraction data to determine a molecular structure of a crystal, the intensity and angular rotation range of a large number of Bragg reflections must be precisely determined. In general, the intensity of a given reflection is spread over several pixels (due to the finite size of the crystal, the divergence of the x-ray beam and the finite resolution of the detector). The reflection is also spread over several adjacent frames (due to the finite angular range over which the crystal diffracts, called the "rocking curve" of the crystal).

Accordingly, in order to generate a three-dimensional molecular model, the data must first be "integrated". The integration process involves converting the series of recorded two-dimensional diffraction patterns or frames, each corresponding to a different crystal orientation, into a three-dimensional model, which in turn involves summing the intensity of a reflection over all the adjacent pixels within a frame and also over all the adjacent frames over which the reflection is spread. This process converts the hundreds of images containing thousands of reflections into a single file. There are a number of techniques for carrying out this integration, but the most powerful is so-called "3D integration". The process of 3D integration of X-ray diffraction data involves two steps. First, the intensity of a given reflection is determined in several frames. This is accomplished either by simple summation of the intensity in a box centered at the predicted reflection position or by fitting a theoretical or experimental profile function to the reflection intensity. The area under this function then gives the integrated intensity for each reflection in the frame.

The second step involves fitting the resulting reflection intensities from adjacent frames to a function in time (or equivalently, to a function in the scan angle, since the scan angle is directly related to time). In particular, the spots for each reflection are distorted over time by their trajectories in the Ewald sphere, which is a well-known geometric construct that relates the wavevector of the incident and diffracted x-ray beams, the diffraction angle for a given reflection and the reciprocal lattice of the crystal. By fitting the intensity in adjacent frames to a function in time based on the Ewald sphere, it is possible to correct for this distortion and thus yield more accurate integrated intensities.

However, in order to process the data with conventional 3D integration software, all the reflections must be synchronized in time. That is, in order to determine 3D fit of each reflection, the integration routines in the software code make an implicit assumption that all the reflections in a given frame are integrated over the exactly the same time period (and thus the same angular range). As this is not true for data acquired in rolling shutter mode as shown in FIG. 3B, the 3D fit for each reflection will be slightly distorted because the reflection intensities will be fitted to an incorrect function in time.

SUMMARY

In accordance with the principles of the invention, by precisely synchronizing the sample rotation with the detector readout, the effects of timing skew on the image intensities and angular positions can be compensated by interpolation or calculation, thus allowing the data to be accurately integrated with conventional software.

In one embodiment, the reflection intensities are interpolated with respect to time to recreate data that is synchronized to a predetermined time. This interpolated data can then be processed by any conventional integration routine to generate a 3D model of the sample.

In another embodiment a 3D integration routine is specially adapted to allow the time-skewed data to be processed directly and generate a 3D model of the sample.

DETAILED DESCRIPTION

In accordance with a first embodiment of the invention, the values of reflection intensities obtained during an actual readout are interpolated in time to calculate intensities which would have been produced by integrating all intensities for equal time periods. This is possible as long as the time interval during which any reflection remains in Bragg resonance is significantly longer than the angular width of a given frame (alternatively, the width (at half height) of the crystal sample rocking curve is substantially wider than the frame width). Typically, this condition implies a frame angular width of less than 0.3 degrees (this condition is often called "fine slicing" or "very fine slicing").

Figure 4:
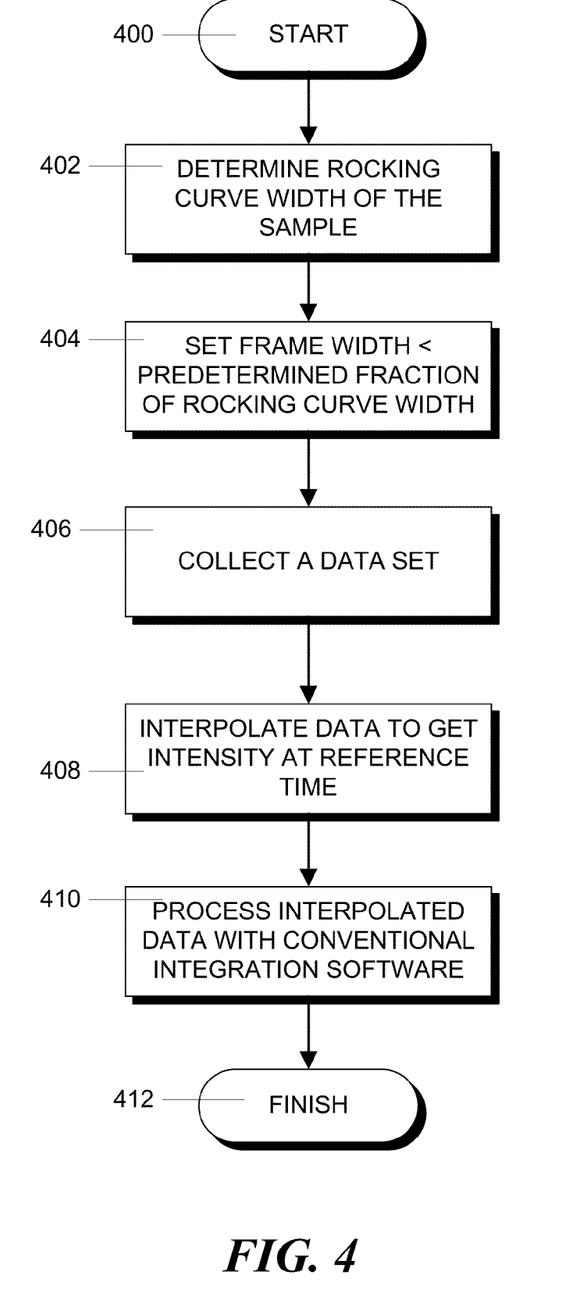
FIG. 4 is a flowchart showing the steps in an illustrative process for correcting rolling shutter timing skew in accordance with a first embodiment of the invention.

The steps comprising this embodiment are shown in FIG. 4. The process begins in step 400 and proceeds to step 402. Since the data must be acquired such that the width of each frame is less than the width of the rocking curve of the sample, in step 402, the sample crystal rocking curve width is determined. This width can be determined by taking several frames of data with very small frame widths (for example, 0.1 degrees). The width (at half height) of the rocking curve from several reflections appearing in the frames can then be determined and averaged to determine the required rocking curve width.

Next, in step 404, the frame width which will be used to acquire an entire data set is set to a predetermined fraction of the determined rocking curve width. This predetermined fraction should be less then 0.5 of the rocking curve width and may, for example, be 0.25 of the rocking curve width. For example, if the width of the rocking curve is 0.6 degrees, the frame width might be set to one quarter of the rocking curve width or about 0.15 degrees or less. This requires that the entire data collection system, including the detector and the goniometer, be optimized to permit accurate fine slicing. Also, the rotation of the goniometer must be precisely synchronized with the readout of the detector. If these conditions can be met, then in step 406, a complete crystallographic data set is acquired using a detector with a rolling shutter mode and the frame width set in step 404.

After the data set is acquired, the reflections are synchronized in step 408 by replacing the intensity value of each pixel by an intermediate intensity value calculated at a reference time occurring at the middle of the frame readout time. This is done as follows. Consider a particular pixel, j, and two adjacent frames, i and i+1, then the readout will produce two data points, one for intensity, $I_{j,i}$ which was read at time $t_{j,i}$ and also one for the intensity from the subsequent frame, $I_{j,i+1}$ which was read at time $t_{j,i+1}$. Ideally, it would be desirable to know the intensity at pixel j at some reference time, $t_{ref}$ that lies between the two readout times, that is, $t_{j,i} > t_{ref} > t_{j,i+1}$ (for all j) where the relative location of $t_{ref}$ between $t_{j,i}$ and $t_{j,i+1}$ is the same for all pixels. This intensity is shown schematically in FIG. 5 which is a schematic plot of incident X-ray intensity on the vertical axis versus time on the horizontal axis. The X-ray intensity that would have been observed at a given reference time, $t_{ref}$, 500 can be found by interpolating between the X-ray intensity values 502 and 504 that actually were observed in two or more adjacent frames.

Figure 5:
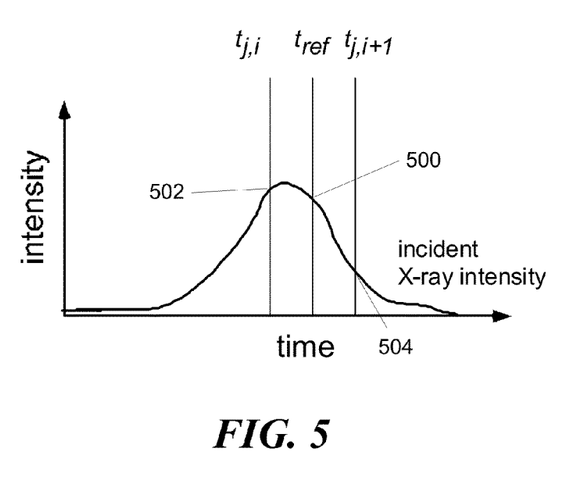
FIG. 5 is a schematic plot of incident X-ray intensity on the vertical axis versus time on the horizontal axis for a single Bragg reflection.

For example, the intensity that would have been measured at a time $t_{ref}$ can be estimated by simple linear interpolation between the two actual measurements as set forth in the following formula:

$$I_j(t_{ref}) = I_j(t_{j,i}) + \frac{[I_j(t_{j,i+1}) - I_j(t_{j,i})]}{(t_{j,i+1} - t_{j,i})}(t_{ref} - t_{j,i})$$

This linear interpolation is only approximate and will only be accurate as long as the readout time is short compared to the time that the Bragg reflection is in resonance.

Of course, the "excess signal" $I_{j,i}^{excess}(t_{j,i+1}) = I_j(t_{j,i+1}) - I_j(t_{ref})$ not be assigned to the current frame would then be stored as the starting signal for the next frame (for the special case of the first frame in a series then the excess signal is zero, that is, $I_{j,0}^{excess}(t_{j,0})=0$).

Including this excess charge from the previous frame then the interpolated frame intensity is given by:

$$I_j(t_{ref}) = I_j(t_{j,i}) + \frac{[I_j(t_{j,i+1}) - I_j(t_{j,i})]}{(t_{j,i+1} - t_{j,i})}(t_{ref} - t_{j,i}) + I_j^{excess}(t_{j,i})$$

Thus, the interpolation does not create or destroy any X-ray signal.

A more accurate interpolation may be achieved by using a higher order fit, for example, a 3-point Lagrange interpolation can be used to yield a more accurate result. In this case three adjacent frames, i−1, i and i+1 are interpolated and the interpolated intensity at pixel j at a time $t_{ref}$ is given by:

$$I_j(t_{ref}) = \frac{(t_{ref} - t_{j,i-1})(t_{ref} - t_{j,i+1})}{(t_{j,i-1} - t_{j,i})(t_{j,i-1} - t_{j,i+1})} I_j(t_{j,i-1}) +$$
$$\frac{(t_{ref} - t_{j,i})(t_{ref} - t_{j,i+1})}{(t_{j,i} - t_{j,i-1})(t_{j,i} - t_{j,i+1})} I_j(t_{j,i}) + \frac{(t_{ref} - t_{j,i-1})(t_{ref} - t_{j,i})}{(t_{j,i+1} - t_{j,i})(t_{j,i-1} - t_{j,i+1})} I_j(t_{j,i+1})$$

Other interpolation techniques could be used such as, for example, a spline interpolation. It is not necessary that the frames used in the interpolation be "real" frames. That is, some CMOS sensors have the capability to perform a non-destructive readout (in which the intensity in each pixel is read but the pixel is not reset to zero after the read operation). The interpolation formulae given above assume a normal, destructive readout. However, the interpolating frames (e.g., the frames taken at $t_{i-1}$ and $t_{i+1}$ above) can also be non-destructively read. The advantage with this arrangement is that the interpolation time can be less than the frame time (which in turn reduces the interpolation error).

It is possible to perform this interpolation after data collection in software. However, a preferred implementation stores the data frames locally in the detector electronics and then the interpolation is performed in real time, in the detector electronics (in a FPGA or ALU). Next, in step 410, the data collected in step 406 is processed with conventional integration software to calculate the desired model. The process then ends in step 412.

The advantage of this interpolation approach is that it allows the resulting data to be processed with conventional integration software that implicitly assumes synchronized data. However, the process of interpolation is necessarily approximate and thus introduces some error into the resulting integration. This error may be acceptable as long as the detrimental effect of the interpolation is small compared to the sum of all other error sources.

In accordance with a second embodiment of the invention, an interpolation error is not introduced into the results. As noted above, 3D integration involves fitting the intensities from adjacent frames to a function in time or angle. While all existing integration routines assume that the angular range of each reflection is constant, this assumption is not necessary. Specifically, in accordance with the principles of the invention, the fit is performed on the actual angular range for each reflection.

For example, assume that a particular frame I starts at $t=t_i$ and at a goniometer spindle angle $\phi_i$. The frame is integrated for some integration time, $\Delta t$, during which the sample is rotated through some angular range $\Delta\phi$. The angular range for a reflection centered on a particular pixel j can then be calculated. In particular, the start angle for each pixel j is given by $$\varphi_{j,i} = \varphi_i + \Delta\varphi \frac{t_j}{t_{read}}$$

where $t_j$ is the time at which pixel j is read out (relative to the start of the readout, that is, $t_j = j/N_{pixels} * t_{read}$ with $N_{pixels}$ equal to the total number of pixels in the detector) and $t_{read}$ is the readout time for the detector.

Therefore, since the position j of each reflection is known and the time and angular position for the start of each frame are also known, the actual angular range for each reflection in each individual frame can be precisely calculated. Conventional 3D integration routines can then be used to perform the integration with these corrected angular ranges for each reflection substituted by the spindle angles used in the conventional routines. As an example, one conventional 3D integration routine is described in detail in an article entitled "Evaluation of Single-Crystal X-ray Diffraction Data from a Position-Sensitive Detector", W. Kabsch, *Journal of Applied Crystallography*, v. 21, pages 916-924 (1988) which article is hereby incorporated herein in its entirety by reference. The integration routine described in this article can be used with the spindle angles $\phi$ and $\phi'$ in the rotation equation shown in the article at page 919 replaced by the corrected angles $\phi_{j,i}$ described above. The resulting equation for frame I is:

$$x' = D(u, \phi_{j,i}', \phi_{j,i}) x \approx x + u \times x \sin(\phi_{j,i}' - \phi_{j,i})$$

where the modified spindle angles are defined as set forth above.

Figure 6:
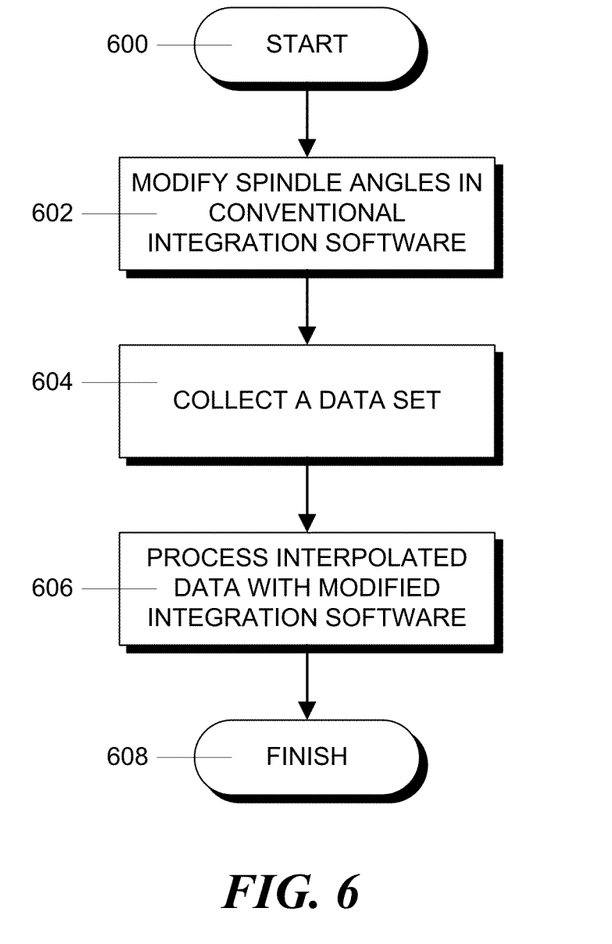
FIG. 6 is a flowchart showing the steps in an illustrative process for correcting rolling shutter timing skew in accordance with a second embodiment of the invention.

FIG. 6 shows the steps in this second embodiment. The process begins in step 600 and proceeds to step 602 where the spindle angles in a selected integration routine are modified as outlined above. Next, in step 604, a data set is collected using a detector in rolling shutter mode. In step 606, the data collected in step 604 is processed with the modified integration software to generate the desired model. The process then finishes in step 608.

While the invention has been shown and described with reference to a number of embodiments thereof, it will be recognized by those skilled in the art that various changes in form and detail may be made herein without departing from the spirit and scope of the invention as defined by the appended claims.

What is claimed is:

1. A method for correcting timing skew in X-ray crystallographic reflection data that is produced by a sample, detected by an X-ray detector that has a plurality of pixels and read out of the detector in a rolling shutter mode, comprising integrating the reflection data with a 3D integration routine in which rotation equations that specify a rotation of a pixel based on a goniometer spindle position have been modified by replacing the goniometer spindle position with a spindle position that depends on the pixel readout time.

2. The method of claim 1 wherein for each pixel j the spindle position $\phi$ in each rotation equation is replaced for frame I by $$\varphi_{j,i} = \varphi_i + \Delta\varphi \frac{t_j}{t_{read}}$$

where $\phi_i$ is the spindle position at the start of frame I, $t_j$ is the time at which pixel j is read out (relative to the start of the readout, that is, $t_j=j/N_{pixels} *t_{read}$ with $N_{pixels}$ equal to the total number of pixels in the detector) and $t_{read}$ is the readout time for the detector.

3. The method of claim 2 wherein the X-ray detector is a CMOS detector.

4. The method of claim 1 wherein the sample is mounted on a rotating goniometer and wherein the method further comprises, before detecting the reflection data, synchronizing the detector readout and the goniometer rotation.

5. The method of claim 1 wherein the X-ray detector comprises a plurality of pixels, each of which detects X-ray crystallographic reflection data and wherein each pixel is reset after data have been readout.

6. The method of claim 1 wherein reflection data is read out of the detector destructively.

7. The method of claim 1 wherein a complete crystallographic dataset is acquired.

8. The method of claim 1 wherein no interpolation error is introduced into the results.

9. A method for correcting timing skew in X-ray crystallographic reflection data that is produced by a sample mounted in a goniometer, detected by an X-ray detector that has a plurality of pixels and read out of the detector in a rolling shutter mode, the method comprising:
   prior to detecting the reflection data, synchronizing the detector readout with a rotation of the goniometer;
   detecting an X-ray reflection signal with the X-ray detector and reading out the reflection data from the detector; and
   integrating the reflection data with a 3D integration routine in which rotation equations that specify a rotation of a pixel based on a goniometer spindle position have been modified by replacing the goniometer spindle position with a spindle position that depends on the pixel readout time.

10. The method of claim 9 wherein for each pixel j the spindle position $\phi$ in each rotation equation is replaced for frame I by $$\varphi_{j,i} = \varphi_i + \Delta\varphi \frac{t_j}{t_{read}}$$

where $\phi_i$ is the spindle position at the start of frame I, $t_j$ is the time at which pixel j is read out (relative to the start of the readout, that is, $t_j=j/N_{pixels} *t_{read}$ with $N_{pixels}$ equal to the total number of pixels in the detector) and $t_{read}$ is the readout time for the $t_{read}$ detector.

11. The method of claim 9 wherein the X-ray detector is a CMOS detector.

* * * * *